(12) United States Patent
Bouduban et al.

(10) Patent No.: US 9,107,745 B2
(45) Date of Patent: Aug. 18, 2015

(54) GRAFT ANCHOR SYSTEM AND METHOD

(71) Applicants: DEPUY SYNTHES PRODUCTS, LLC, Raynham, MA (US); University of Zurich, Zurich (CH)

(72) Inventors: Nicolas Bouduban, Oberdorf (CH); Beat Lechmann, Oberdorf (CH); Patrick Burki, Oberdorf (CH); Jess Snedeker, Zurich (CH); Mazda Farshad, Gockhausen (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 197 days.

(21) Appl. No.: 13/797,421

(22) Filed: Mar. 12, 2013

(65) Prior Publication Data

US 2013/0261677 A1  Oct. 3, 2013

Related U.S. Application Data

(60) Provisional application No. 61/619,705, filed on Apr. 3, 2012.

(51) Int. Cl.
| | |
|---|---|
| *A61B 17/56* | (2006.01) |
| *A61B 17/58* | (2006.01) |
| *A61B 17/064* | (2006.01) |
| *A61B 17/84* | (2006.01) |
| *A61F 2/30* | (2006.01) |
| *A61F 2/08* | (2006.01) |

(52) U.S. Cl.
CPC ....... *A61F 2/0811* (2013.01); *A61F 2002/0835* (2013.01); *A61F 2002/0852* (2013.01); *A61F 2002/0888* (2013.01)

(58) Field of Classification Search
CPC .................................................. A61B 17/0644
USPC .................................. 606/75, 301, 321, 324
See application file for complete search history.

(56) References Cited

U.S. PATENT DOCUMENTS

| | | | |
|---|---|---|---|
| 6,152,928 A | 11/2000 | Wenstrom, Jr. | |
| 6,554,852 B1 * | 4/2003 | Oberlander | 606/232 |
| 7,468,074 B2 | 12/2008 | Caborn et al. | |

(Continued)

FOREIGN PATENT DOCUMENTS

| | | |
|---|---|---|
| EP | 1 332 729 | 8/2003 |
| WO | 02/32345 | 4/2002 |
| WO | 2011/041783 | 4/2011 |

OTHER PUBLICATIONS

International Search Report and Written Opinion (PCT/US2013/034643); Jul. 25, 2013.

*Primary Examiner* — Andrew Yang
(74) *Attorney, Agent, or Firm* — Dunlap Codding, P.C.

(57) ABSTRACT

A graft anchor has first and second arms each having a leading end, a trailing end, an inner surface, and an outer bone contactable surface. The graft anchor also has a resilient bridge extending between the inner surface of the first arm and the inner surface of the second arm to space apart the first arm and the second arm. The resilient bridge defines a graft receiving pathway between the inner surfaces of the first and second arms. The resilient bridge also defines a deflection point about which a force acting upon the resilient bridge in a direction from the leading end to the trailing end causes the leading ends of the first and second arms to move toward one another and the trailing ends of the first and second arms to move away from one another.

13 Claims, 7 Drawing Sheets

(56) References Cited

U.S. PATENT DOCUMENTS

| | | |
|---|---|---|
| 8,591,545 B2 * | 11/2013 | Lunn et al. .................. 606/232 |
| 2003/0171811 A1 | 9/2003 | Steiner et al. |
| 2003/0233095 A1 | 12/2003 | Urbanski et al. |
| 2005/0096743 A1 | 5/2005 | Schmieding et al. |
| 2005/0159812 A1 | 7/2005 | Dinger, III et al. |
| 2007/0032822 A1 * | 2/2007 | Ortiz et al. .................. 606/219 |
| 2007/0225805 A1 | 9/2007 | Schmieding |
| 2009/0054982 A1 | 2/2009 | Cimino |
| 2013/0231667 A1 * | 9/2013 | Taylor et al. .................. 606/75 |

* cited by examiner

GRAFT ANCHOR SYSTEM AND METHOD

INCORPORATION BY REFERENCE

The entirety of U.S. provisional application Ser. No. 61/619,705, filed on Apr. 3, 2012, is expressly incorporated herein by reference.

BACKGROUND

Soft tissues such as tendons and ligaments are generally attached to bones by small collagenous fibers. These fibers are strong, but permit tendons and ligaments to be flexible. When soft tissue is torn away from the bone, a surgeon is often required to reattach the soft tissue, or a replacement tissue graft to the bone with one of more surgical anchors or other surgical fixation implants. Surgical fixation implants, such as screws, surgical anchors, graft anchors, and surgical pins, may be implanted into a patient's bone to reattach or fix soft tissue or to reinforce damaged bone. Fixation implants are implanted into bone using extensive surgical procedures, and more recently, using arthroscopic surgical techniques. A growing recent trend is to manufacture fixation implants from bio-inert and bio-absorbable materials so that native bone tissue may gradually absorb the fixation implant and grow into the space occupied by the fixation implant to replace the implant with native bone tissue.

A frequently performed procedure where fixation implants are routinely used to attach a ligament graft to a bone is anterior cruciate ligament (ACL) reconstruction. This procedure generally involves removing the torn or damaged ACL and forming tunnels in the distal femur and proximal tibia in close proximity to the original ACL attachments sites. A replacement graft may be harvested from the patellar tendon (along with a portion of the patella and the tibia, i.e., a bone-to-bone graft), from the hamstring tendons of the patient, or from another donor. The graft may be pulled through or into the bone tunnels and fixed in the bone tunnels with a graft anchor. The graft may then be left to function as a new ACL. The tibial portal is more commonly used for this procedure, but the antero-medial portal has seen some increased use recently.

Rigid fixation of the graft anchor is recognized as an important factor for the long-term success of ACL reconstruction procedures. Rigid fixation is difficult to initially obtain, and even more difficult to maintain throughout the life of the graft anchor.

One type of graft anchor commonly used to fix the ligament graft in ACL reconstructions is an interference screw, which biases a graft segment, against a wall of a bone tunnel (e.g., formed in the femur). However, use of interference screws may result in damage to the graft. For example, the threads of the interference screw, and the bone tunnel wall may cut or abrade the graft as the interference screw is advanced into the bone tunnel. Further, advancing the interference screw into the bone tunnel over the graft may twist the graft in a way that proper graft tension is lost or exceeded. In more severe cases, over-tightening of the interference screw may cause catastrophic failure of the bone tunnel known as tunnel blowout.

Tunnel sealing is another important consideration in ACL reconstructions, as it is known that synovial fluid acting on the interference screw may cause bone tunnel enlargement. For example, improper tunnel sealing may result in graft loosening, such as a bungee effect or windshield wiper effect.

Attempts have been made to overcome the above deficiencies in the prior art. However, such attempts involve multi-piece fixation implants which require forming additional holes or tunnels into the bone (e.g., transversely to the initial attachment tunnel), and thus result in increased procedure duration and complexity, implant costs, surgeon errors and failure rates, and prolong patient recovery time.

BRIEF DESCRIPTION OF THE DRAWINGS

To assist those of ordinary skill in the relevant art in making and using the inventive concepts disclosed herein, reference is made to the appended drawings and schematics, which are not intended to be drawn to scale, and in which like reference numerals may refer to the same or similar elements for consistency. For purposes of clarity, not every component may be labeled in every drawing. Certain features and certain views of the figures may be shown exaggerated in scale or in schematic in the interest of clarity and conciseness. In the drawings.

DETAILED DESCRIPTION OF EXEMPLARY EMBODIMENTS

Before explaining at least one embodiment of the inventive concepts in detail, it is to be understood that the inventive concepts disclosed herein are not limited in their application to the details of construction, experiments, exemplary data, and the arrangement of the components set forth in the following description or illustrated in the drawings. The inventive concepts are capable of other embodiments or being practiced or carried out in various ways. Also, it is to be understood that the phraseology and terminology employed herein is for purposes of description and should not be regarded as limiting.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, certain well-known features may not be described in detail to avoid unnecessarily complicating the instant disclosure.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

The term "and combinations thereof" as used herein refers to all permutations or combinations of the listed items preceding the term. For example, "A, B, C, and combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. A person of ordinary skill in the art will understand that typically there is no limit on the number of items or terms in any combination, unless otherwise apparent from the context.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The use of the terms "at least one" and "one or more" will be understood to include one as well as any quantity more than one, including but not limited to each of, 2, 3, 4, 5, 10, 15, 20, 30, 40, 50, 100, and all integers and fractions, if applicable, therebetween. The terms "at least one" and "one or more" may extend up to 100 or 1000 or more, depending on the term to which it is attached; in addition, the quantities of 100/1000 are not to be considered limiting, as higher limits may also produce satisfactory results.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, and combinations thereof, for example.

Further, as used herein, the term "patient" is meant to include all organisms, whether alive or dead, including all species of animals. For example, a graft anchor system according to the inventive concepts disclosed herein may be used to treat a detachment, tear, or other soft tissue injury, in a human being, a horse, a cow, a sheep, a cat, a dog, and other organisms. As another example, a graft anchor according to the instant disclosure may be used in a non-living human cadaver or other appropriate natural or artificial model to train medical or veterinary personnel in surgical techniques. As yet another example, a graft anchor system according to the inventive concepts disclosed herein may be used to implant other medical devices such as replacement joints, pacemakers, and the like, into an organism, by anchoring or fixing such medical devices to a bone. As yet another example, a method according to the inventive concepts disclosed herein may be used to repair rotator cuff instabilities and tears in shoulder surgery, or to repair various knee, elbow, hip, wrist, ankle, or other soft tissue tears or detachments and joint injuries.

Also, as used herein the terms graft, grafts, graft loop, and any variations thereof, are intended to include natural materials, such as tendons, ligaments, connective tissue, collagen fibers, and combinations thereof, and encompassing autografts, allografts, and xenografts (or heterografts). Further, said terms include synthetic substitutes for ligaments and tendons, and combinations of natural materials and synthetic substitutes, for example. Synthetic substitutes may include metallic materials, ceramics, polymeric materials, fibrous braid implants, implants comprised of textiles or fabrics, and combinations thereof, for example. Finally, said terms include a combination of natural materials and synthetic substitutes, and comprise a graft, a graft loop, and a graft bundle, and combinations thereof, for example.

The inventive concepts disclosed herein will be described in connection with ACL reconstruction. It is to be understood that, while this description relates to the attachment of a ligament graft to a femur and a tibia located within a knee of a patient, the inventive concepts disclosed herein are not limited to ACL reconstruction procedures. A graft anchor, a graft anchor system, and a method according to the inventive concepts disclosed herein may be used to fix or secure a ligament, a tendon, or other soft tissue, to any bone, whether such ligament, tendon, or soft tissue is secured with the use of sutures or not.

The inventive concepts disclosed herein are generally directed to a graft anchor system for anchoring a graft into a bone tunnel and to a method of using same. The graft anchor system includes a graft anchor which may be generally cylindrical and comprises a pair of arms supported in a spaced apart relationship by a resilient bridge. The arms have a trailing end, a leading end, and an outer side configured to conform to the contour of a bone tunnel. The bridge has inwardly curved sides and an inwardly curved distal side cooperating with the arms to define a graft receiving pathway. The graft receiving pathway is configured to allow a portion of the graft to contact the bone tunnel. A graft may be inserted into the graft receiving pathway such that the graft loops around the graft anchor. The graft anchor may then then inserted into a bone tunnel and retained inside the bone tunnel via a combination of scissor-like pivoting motion of the arms about the bridge and bone engaging and/or retention features formed on the outer sides of the arms, as will be described below.

Referring now to the drawings, and in particular to FIGS. 1-4, a graft anchor 100 according to the inventive concepts disclosed herein is shown. The graft anchor 100 generally includes a first arm 102a and a second arm 102b supported in a spaced-apart relationship by a bridge 104.

In the exemplary embodiment, the first arm 102a and the second arm 102b are shown as substantially identical in structure and function. It is to be understood, however, that while the first arm 102a and second arm 102b are shown to allow for a symmetrical engagement of the graft anchor 100 into a bone tunnel, in some exemplary embodiments, the first arm 102a and the second arm 102b may be implemented differently from one another, such as by having different sizes, different surface features, or by being made of different materials, for example. Further, in some exemplary embodiments, the graft anchor 100 may be implemented with more than two arms.

The first arm 102a has a trailing end 106a, a leading end 108a, an inner side or surface 110a, an outer side 112a, and a length 114a extending from the trailing end 106a to the leading end 108a. The leading end 108a of the first arm 102a may be tapered to allow for easier insertion of the graft anchor 100 into a bone tunnel, for example.

The outer side 112a is configured to substantially conform to the contour of a bone tunnel along the length 114a of the first arm 102a. The outer side 112a is shown as having a substantially cylindrical shape configured to conform to the contour of a substantially cylindrical bone tunnel as will be described in detail below. It is to be understood that the outer side 112a may have any other suitable form configured to conform to the contour of a bone tunnel, such as oval, elliptical, irregular, and combinations thereof, for example.

The outer side 112a may further include one or more serrations 116a formed thereon and configured for gripping engagement with a femoral bone tunnel. It is to be understood that, while the outer side 112a is shown as having serrations 116a formed thereon, in some exemplary embodiments only a part of the outer side 112a may have serrations 116a, and a part of the outer side 112a may lack serrations 116a. Further, in some exemplary embodiments other retention structures, such as grooves, threads, spikes, bumps, striations, barbs, pins, knurls, and combinations thereof may be implemented, instead of, or in combination with serrations 116a.

The outer side 112a may be further provided with one or more bone-engaging protrusions 120a extending therefrom and configured to engage a portion of the femoral bone tunnel. In an exemplary embodiment, the bone-engaging protrusion 120a extends at an angle α (FIG. 2) relative to the outer side 112a in a direction from the leading end 108a to the trailing end 106a. The angle α may vary from approximately 0° to approximately 90°, for example. In an exemplary embodiment, the angle α may be approximately 30°. The bone-engaging protrusion 120a may be sized such that the bone-engaging protrusion 120a does not extend past the trailing end 106a of the first arm 102a. An end of the bone-engaging protrusion 120a may finish a predetermined distance before the trailing end 106a. The predetermined distance may be chosen so that the bone-engaging protrusion 120a passes through the cancellous bone and contacts the cortical bone surrounding an entrance into the femoral bone tunnel to achieve so called "aperture fixation" when the graft anchor 100 is inserted into the femoral bone tunnel. The predetermined distance may be in a range of 2 mm to 4 mm and could be chosen according to the type of person in which the graft anchor is to be implanted. For example, in an averaged-sized Caucasian male, the distance may be about 4 mm and, in an average-sized Asian female, the distance may be about 2 mm.

In one version, the bone-engaging protrusion 120a may be configured in the operating room by a surgeon to have an appropriate predetermined distance. In another version, a range of graft anchors may be provided having, for example, a predetermined distance of 2 mm, 3 mm, and 4 mm, so that a surgeon may select a graft anchor according to a determination of the size of the cortical bone of the patient. Also, the bone-engaging protrusion 120a may be constructed of a resilient material such that the bone-engaging protrusion 120a is pressed substantially flat against the outer side 112a as the graft anchor 100 is inserted into the femoral bone tunnel, but extend outwards when tension is applied to the graft anchor 100 to prevent backing-out of the graft anchor 100, for example.

One or more openings 124a may be formed in the first arm 102a such that the openings 124a extend through the first arm 102a from the inner side 110a to the outer side 112a. The openings 124a may be configured to receive one or more sutures (not shown) or suture loops (not shown) therein. It is to be understood that in some exemplary embodiments, the openings 124a may be implemented as notches, hooks, or slits, for example. The openings 124a may be formed into the first arm 102a in any suitable manner, and may function to allow one or more sutures or suture loops to be inserted therein, so that the graft anchor 100 may be pulled or guided by the sutures into the femoral bone tunnel as will be described below.

Figure 1:
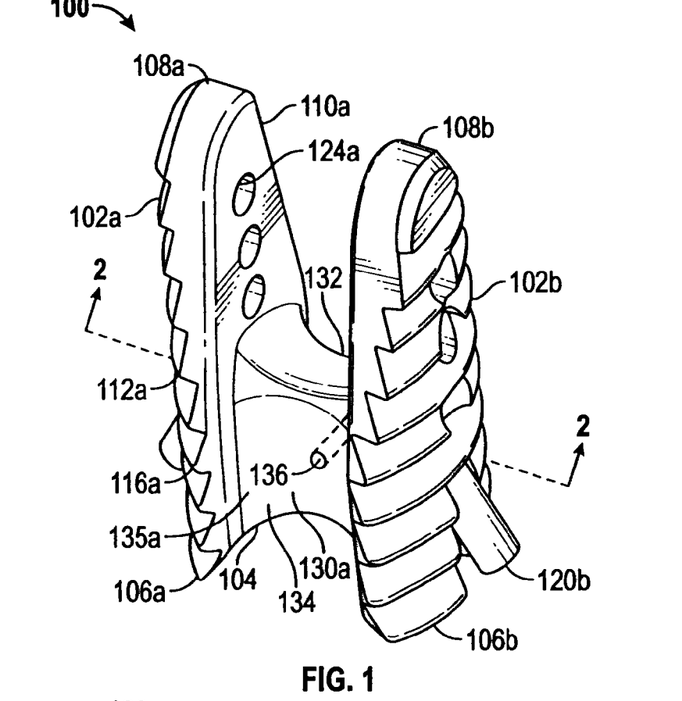
FIG. 1 is a perspective view of an exemplary embodiment of a graft anchor according to the inventive concepts disclosed herein.
Figure 3A:
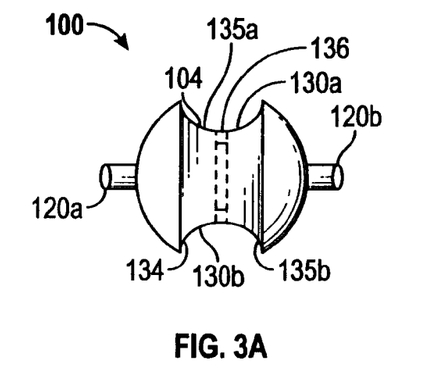
FIG. 3A is a bottom plan view of the graft anchor of FIG. 1.
Figure 3B:
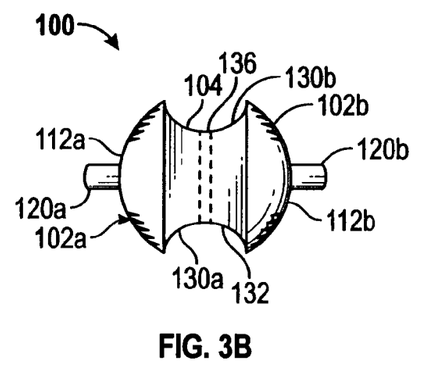
FIG. 3B is a top plan view of the graft anchor of FIG. 1.
Figure 4:
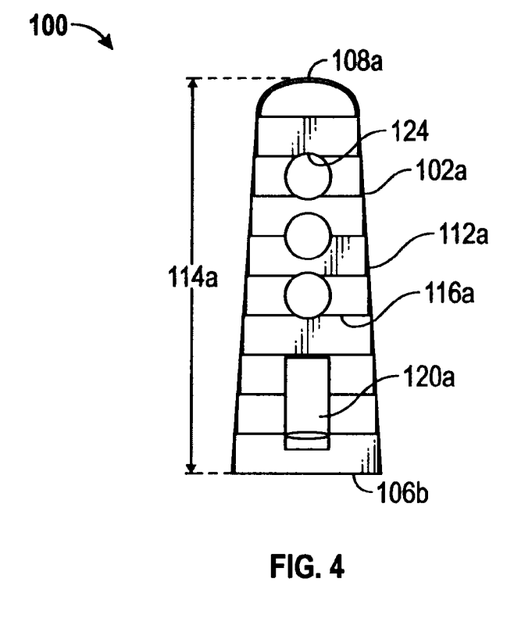
FIG. 4 is a side elevational view of the graft anchor of FIG. 1.

The openings 124a may also serve to facilitate bone tissue integration into the graft anchor 100. It is to be understood that while three openings 124a are shown in the first arm 102a, some embodiments may include only one opening, two openings, or more than two openings, for example. Further, while the one or more openings 124a are shown as being aligned, it is to be understood that in some embodiments the openings 124a may be staggered, or offset.

The second arm 102b may be implemented and may function substantially similarly to the first arm 102a, and thus includes a trailing end 106b, a leading end 108b, an inner side or surface 110b, an outer side 112b, and a length 114b extending from the trailing end 106b to the leading end 108b. It is to be understood that in some exemplary embodiments, the second arm 102b may be implemented differently from the first arm 102a, such as for example, by having a different length, different bone-retention features, different arrangement, and number of openings 124b, and combinations thereof.

The bridge 104 has an inwardly curved first side or surface 130a, an inwardly curved second side or surface 130b, and an inwardly curved distal side 132. The bridge 104 extends between the inner side 110a of the first arm 102a and the inner side 110b of the second arm 102b so as to support the first arm 102a and the second arm 102b in a spaced apart relationship with the outer side 112a of the first arm 102a and the outer side 112b of the second arm 102b in an opposing relationship relative to one another. The inwardly curved first side 130a, the inwardly curved second side 130b, and the inwardly curved distal side 132 cooperate with the first arm 102a and the second arm 102b to define a smooth graft receiving surface and a graft receiving pathway 134. In one version, the graft receiving pathway 134 has a predetermined sealing dimension selected according to the size of the graft. The graft receiving pathway 134 has a first channel 135a and a second channel 135b. The first channel 135a is defined by the inner surfaces 110a and 110b of the first and second arms 102a and 102b, and the first surface 130a of the resilient bridge 134. The second channel 135b is defined by the inner surfaces 110a and 110b of the first and second arms 102a and 102b, and the second surface 130b of the resilient bridge 134. The sealing dimensions of the first and second channels 135a and 135b are chosen to receive a graft therein in such a way that the graft and the graft anchor 100 cooperate to form a seal in the entrance of a bone tunnel in a manner to be discussed below.

The distal side 132 of the bridge 104 defines a bearing surface between the first channel 135a and the second channel 135b. The bridge 104 is constructed of a resilient and flexible material, such that the bridge 104 may deform, flex, or compress, under pressure (represented by arrow 105 in FIG. 2) to allow the leading end 108a of the first arm 102a and the leading end 108b of the second arm 102b to move toward one another (represented by arrows in FIG. 2), and to allow the trailing end 106a of the first arm 102a, and the trailing end 106b of the second arm 102b to move away from one another (represented by arrows in FIG. 2) when a tensile force is applied to a graft positioned in the graft receiving pathway 134, to enhance the fixation of the graft anchor 100 into the bone tunnel, as will be described below.

Figure 2:
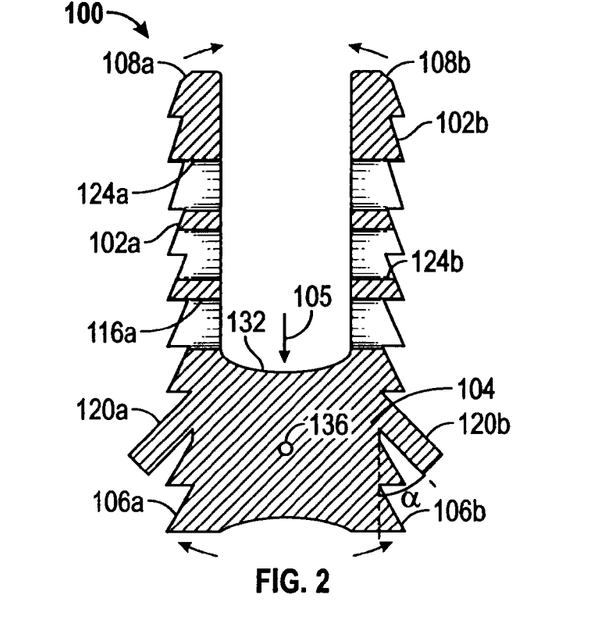
FIG. 2 is a cross-sectional view taken along line 2-2 of FIG. 1.

The bridge 104 may further include one or more synovial fluid drain 136 formed therein such that the inwardly curved first side 130a is in fluid communication with the inwardly curved second side 130b to allow any synovial fluid to flow from the inwardly curved first side 130a and the inwardly curved second side 130b. It is to be understood, however, that in some embodiments the synovial fluid drain 136 may be omitted, for example, or two, three, or more synovial fluid drains 136 may be implemented. Further, while the synovial fluid drain 136 is shown as being substantially cylindrical in shape, the synovial fluid drain 136 may be implemented as oval, square, polygonal, star-shaped, and combinations thereof, or may have any other suitable shape, for example.

The graft anchor 100 may be made of any suitable material or combinations of materials including resorbable and non-resorbable polymers, such as polyethylene, polypropylene, ultra high molecular weight polyethylene, poly-ether-ether-ketone (PEEK), poly-ether-ketone-ketone (PEKK), resorbable polymers, such as poly-lactic acid (PLA), poly-L-lactide (PLLA), poly-L/D-lactide (PLDLA), poly-lactic-co-glycolic acid (PLGA), poly-glycolide or poly-glycolic acid (PGA), poly-capro-lactone (PCL), or soft metals, such as nitinol. The graft anchor 100 may be uncoated, coated, or impregnated with various substances, such as for example antibiotics, titanium, titanium modified with an anodic plasma-chemical (APC) process, and combinations thereof, for example. The graft anchor 100 may be constructed using any desired methods, such as injection molding, casting, machining, molding, thermoplastic setting, 3D printing, and combinations thereof, for example.

Figure 5:
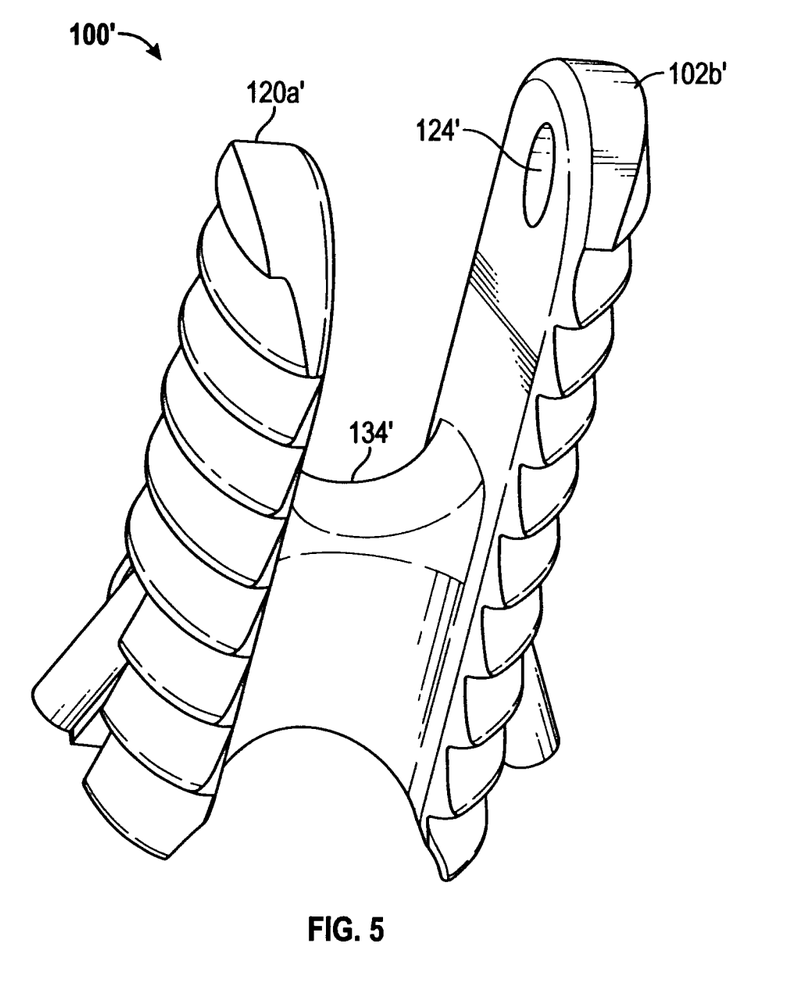
FIG. 5 is a perspective view of another exemplary embodiment of a graft anchor according to the inventive concepts disclosed herein.

Referring now to FIG. 5 a second embodiment of a graft anchor 100' according to the inventive concepts disclosed herein is shown. The graft anchor 100' has all features in common with the graft anchor 100, with the exception that the first arm 102a' is shorter in length than the second arm 102b'. For example, the first arm 102a' is between about 1 mm and about 15 mm shorter than the second arm 102b'. Other differences in arm length are of course possible, as the skilled person would appreciate. The first arm 102a', which is shortened, may facilitate easier catching of a graft. During surgery, a suture will be positioned in the bone tunnel in the femur for guiding the graft anchor 100' into the bone tunnel, for example. The suture may then be positioned to pass through a loop formed in the graft. This suture is inserted through an opening 124' formed in the graft anchor 100'. The graft anchor 100' is then guided into position in the bone tunnel by sliding it along the suture. Along its route to the bone tunnel, the graft anchor 100' may come into contact with the graft. In particular, an internal surface of the arm 102b' may contact the graft first, which guides the graft into the space between the first arm 102a' and the second arm 102b' (or the graft receiving pathway 134'), where the graft is anchored after implantation.

Figure 6A:
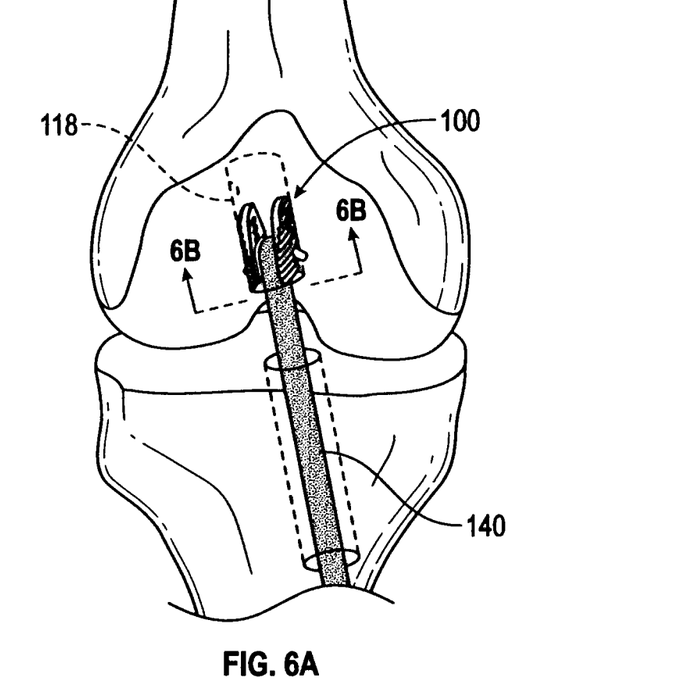
FIG. 6A is a diagrammatic view of a femoral tunnel with a graft anchor and graft loop inserted therein.
Figure 6B:
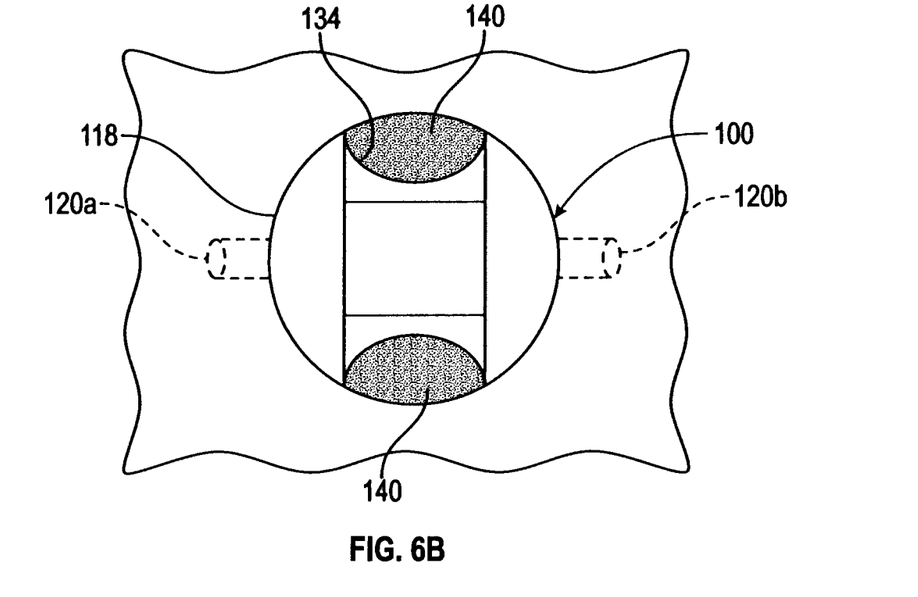
FIG. 6B is a sectional view taken along line 6B-6B of FIG. 6A.

Referring now to FIGS. 6A-6B, the graft anchor 100 is shown positioned inside a femoral bone tunnel 118 with a graft 140 positioned in the graft receiving pathway 134 such that at least a portion of the graft 140 is in contact with the bridge 104 and with the femoral bone tunnel 118, for example. As shown in FIG. 6B, the graft anchor 100 cooperates with the graft 140 to substantially seal the femoral bone tunnel 118 such that at least a portion of the graft 140 is maintained in contact with the femoral bone tunnel 118 to facilitate attachment of the graft 140 to the bone tissue inside the femoral bone tunnel 118.

The graft anchor 100 is designed to be atraumatic, i.e., to minimize the damage and pressure exerted by the graft anchor 100 to the femoral bone tunnel 118 and to the graft 140. For example, the graft anchor 100 is designed to exert symmetrical pressure on the femoral bone tunnel 118, and such pressure is spread out over the outer side 112a and the outer side 112b to minimize the chance of femoral bone tunnel 118 enlargement or blowout. Further, the graft receiving pathway 134 is designed to protect the graft 140 from damage during the insertion of the graft anchor 100 into the femoral bone tunnel 118, while at the same time maximizing the contact surface between the femoral bone tunnel 118 and the graft 140. Further, the openings 124a and 124b may serve to accelerate bone tissue integration of the graft anchor 100 by providing spaces to encourage bone ingrowth into the graft anchor 100. Even further, the bone-engaging protrusions 120a and 120b are sized and positioned such that the bone-engaging protrusions 120a and 120b extend into the cancellous portion of the bone and beneath the cortical portion of the bone to preserve the integrity and mechanical strength of the cortical portion of the bone surrounding the femoral bone tunnel 118 and to further minimize the risks for tunnel enlargement and blowouts, for example.

Figure 7:
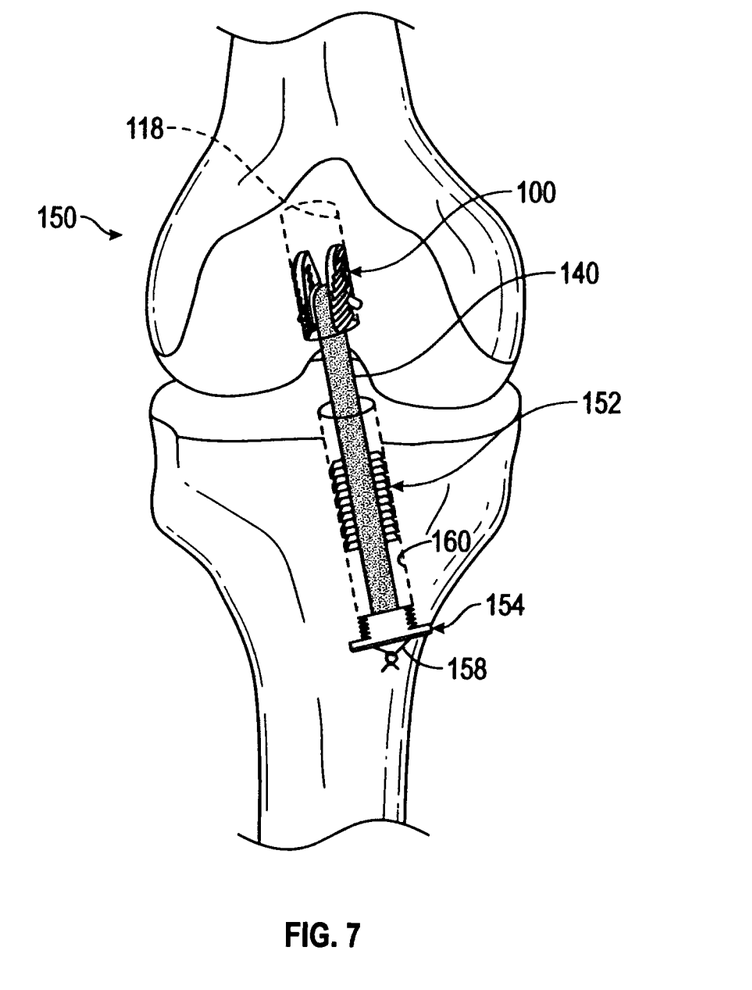
FIG. 7 is a diagrammatic view of an exemplary embodiment of an ACL reconstruction using a graft anchor system according to the inventive concepts disclosed herein.

Referring now to FIG. 7 shown therein is a graft anchor system 150 according to an exemplary embodiment of the inventive concepts disclosed herein. The graft anchor system 150 comprises a graft anchor 100, a tibial graft spacer 152, and a tibial fixation implant 154. The graft anchor 100 is inserted into a femoral bone tunnel 118, and secures a graft 140 inside the femoral bone tunnel 118. The tibial graft spacer 152 is inserted into a tibial bone tunnel 160 and guides the graft 140 through the tibial bone tunnel 160. The tibial fixation implant 154 is inserted into an end of the tibial bone tunnel 160 and anchors one or more sutures 158 attached to the graft 140 such that appropriate tension is maintained on the graft 140.

Figure 8:
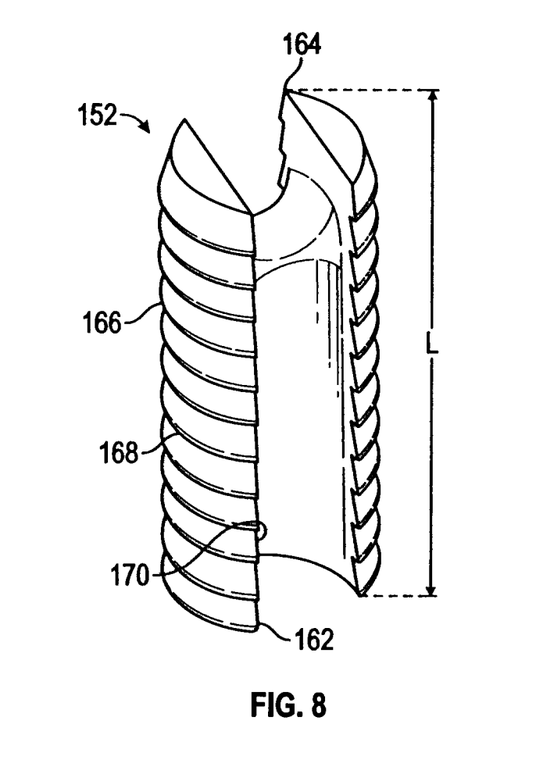
FIG. 8 is a perspective view of an exemplary embodiment of a tibial graft spacer according to the inventive concepts disclosed herein.

Referring now to FIG. 8, the tibial graft spacer 152 comprises a first end 162, a second end 164, and an outer side 166. The outer side 166 extends a length L from the first end 162 to the second end 164 and is configured to substantially conform to the contour of the tibial bone tunnel 160, and is provided with serrations 168 for engaging the tibial bone tunnel 160 so as to retain the tibial graft spacer 152 inside the tibial bone tunnel 160. The outer side 166 further defines one or more inwardly curved grooves 170 extending from the first end 162 to the second end 164 thereof. The grooves 170 are configured to receive and retain at least a portion of the graft 140 therein.

The tibial graft spacer 152 may include one or more synovial fluid drains (not shown) to allow fluid communication between the grooves 170. The tibial graft spacer 152 is configured to guide the graft 140 in the tibial bone tunnel 160 such that at least a portion of the graft 140 is maintained in contact with the tibial bone tunnel 160 when the tibial graft spacer 152 and graft 140 are inserted therein and thereby allow the graft 140 to attach to the bone tissue inside the tibial bone tunnel 160.

It is to be understood that in some exemplary embodiments of the inventive concepts disclosed herein, two or more than two tibial graft spacers 152 may be implemented depending on the length of the tibial bone tunnel 160 and the length of the tibial graft spacers 152. Further, in some exemplary embodiments of the inventive concepts disclosed herein, the tibial graft spacer 152 may be omitted. The tibial graft spacer 152 may be made of similar materials and using similar techniques as the graft anchor 100.

Figure 9:
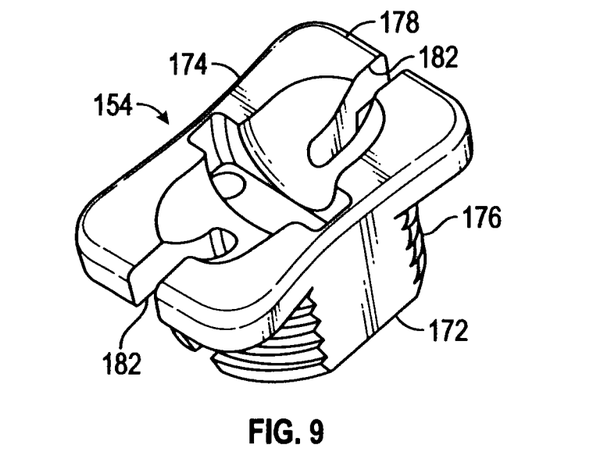
FIG. 9 is a perspective view of an exemplary embodiment of a tibial fixation button according to the inventive concepts disclosed herein.

Referring now to FIG. 9, the tibial fixation implant 154 comprises a first end 172, a second end 174, an outer side 176 configured to conform to the contour of the tibial bone tunnel 160, and a flange 178 having a diameter larger than the diameter of the tibial bone tunnel 160. The outer side 176 is configured to be inserted into the tibial bone tunnel 160 and is provided with serrations 180 configured to engage the tibial bone tunnel 160 and retain the tibial fixation implant 154 therein. The outer side 176 further has one or more suture notches 182 formed therein and configured to allow for one or more sutures 158 (FIG. 7) attached to the graft 140 to extend at least partially therethrough so that the sutures 158 may be used to anchor the graft 140 to the tibial fixation implant 154 and impart an appropriate tension thereto. The sutures 158 may be anchored by the tibial fixation implant 154 by passing the sutures 158 through the suture notches 182 and tying off the sutures 158 at the appropriate tension. The flange 178 may rest against the surface of the tibia when the tibial fixation implant 154 is inserted into the tibial bone tunnel 160 and may function to prevent the tibial fixation implant 154 from migrating into the tibial bone tunnel 160 when tension is applied to the tibial fixation implant 154 by the sutures 158. The tibial fixation implant 154 may be constructed and implemented similarly to the graft anchor 100, and may be constructed of PEEK, for example.

Figure 10A:
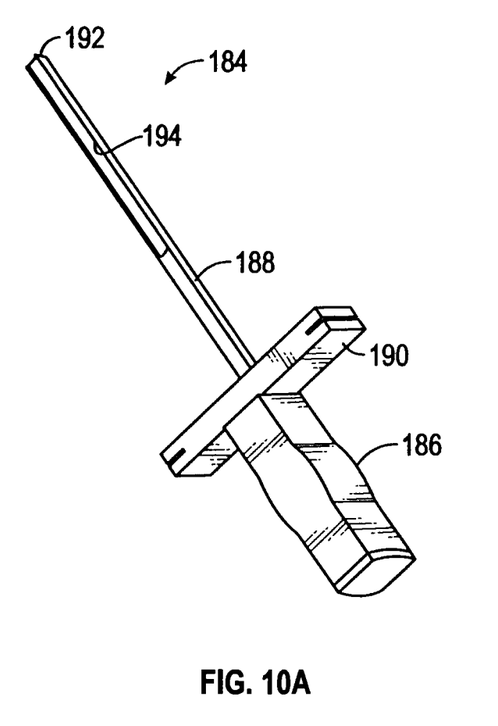
FIG. 10A is a perspective view of an insertion tool constructed according to the inventive concepts disclosed herein.
Figure 10B:
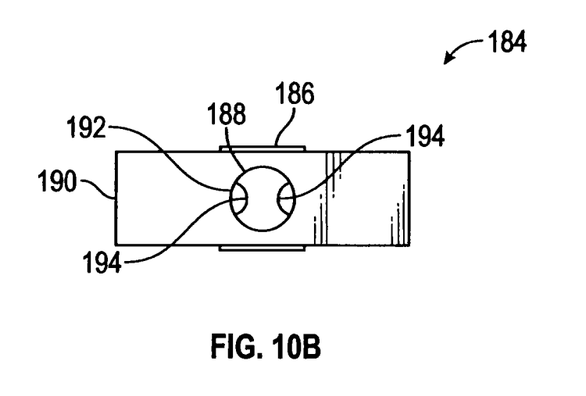
FIG. 10B is an end view of the insertion tool of FIG. 10A.

Referring now to FIGS. 10A-10B, shown is an exemplary embodiment of an insertion tool 184 which may be employed to insert the graft anchor 100 and the tibial graft spacer 152 into a respective bone tunnel according to the inventive concepts disclosed herein. The insertion tool 184 may comprise a handle 186 and a shaft 188 extending longitudinally from the handle 186. The insertion tool 184 is configured to allow a user, such as a surgeon or a surgical robot, for example, to push, press, or otherwise insert the graft anchor 100 into a bone tunnel, as will be described below. The insertion tool 184 may also be used in conjunction with a navigation system.

The handle 186 may be implemented as a conventional surgical instrument handle and may comprise grip-enhancing features, such as rubberized portions, grooves, striations, bumps, knurls, and combinations thereof, for example. The handle 186 may comprise a suture collar 190 configured to receive and retain one or more sutures therein such that the graft 140 may be manipulated via one or more sutures 158 (FIG. 7) attached to the graft 140 during the insertion of the graft anchor 100 and the tibial graft spacer 152 into the respective bone tunnels 118 and 160.

The shaft 188 may comprise a tip 192 and may have one or more inwardly curved graft grooves 194 extending at least partially along the length of the shaft 188 and configured to receive at least a portion of the graft 140 therein during the use of the insertion tool 184. The shaft 188 is configured such that the tip 192 corresponds to and contacts the graft anchor 100, but does not contact the graft 140 to avoid damage to the graft 140 by the tip 192. A suture attached to the graft 140 may be used to guide the graft 140 away from the tip 192 and secure the graft 140 by securing the one or more sutures in the suture collar 190, for example. Similarly, the tip 192 is configured to contact the first end 162 and/or the second end 164 of the tibial graft spacer 152 without damaging the graft 140 to insert the tibial graft spacer 152 inside the tibial bone tunnel 160 and/or adjust the position of the tibial graft spacer 152 inside the tibial bone tunnel 160, for example.

In some exemplary embodiments, the insertion tool 184 may be cannulated such that a guide wire (not shown) may be used to guide the insertion tool 184 into the femoral bone tunnel 118 or the tibial bone tunnel 160, while in other exemplary embodiments the insertion tool 184 may be non-cannulated.

It is to be understood that any suitable surgical tool may be used to insert the graft anchor 100, the tibial graft spacer 152, and the tibial fixation implant 154 into a bone tunnel. Further, a first surgical tool maybe used to insert the graft anchor 100 in the femoral bone tunnel 118, a second surgical tool may be used to insert the tibial graft spacer 152 into the tibial bone tunnel 160, and a third surgical tool may be used to insert the tibial fixation implant 154 into the tibial bone tunnel 160, for example.

In use, a method for ACL replacement using the graft anchor system 150 according to the inventive concepts disclosed herein comprises capturing a graft 140 with a graft anchor 100. Capturing the graft 140 may comprise inserting a portion of the graft 140 into the graft receiving pathway 134 of the graft anchor 100. In one version, the graft receiving pathway 134 is sized such that the graft 140 and the graft anchor 100 cooperate to form a seal in the bone tunnel 118 (FIG. 6B). Additionally, one or more sutures may be passed through one or more of the openings 124a and 124b formed in the first arm 102a and the second arm 102b respectively, for example. Such sutures may be inserted prior to, simultaneously with, or after, capturing the graft 140 into the graft receiving pathway 134, and may function to secure the graft 140 in the graft receiving pathway 134. Such sutures may further be used to guide the graft anchor 100 toward, or into, the femoral bone tunnel 118, for example.

The insertion tool 184 may be used to insert the graft anchor 100 into the femoral bone tunnel 118 such that the graft anchor 100 sits substantially level with the surface of the femur, extends slightly above the surface of the femur, or sits slightly below the surface of the femur, for example. The graft 140 desirably extends through the graft receiving pathway 134 and past the trailing end 106a of the first arm 102a and the trailing end 106b of the second arm 102b.

The tibial graft spacer 152 may be inserted in the tibial bone tunnel 160 via the insertion tool 184, and the graft 140 may be guided into the tibial bone tunnel 160 and at least partially into the one or more grooves 170, such that the graft 140 extends past the second end 164 of the tibial graft spacer 152, for example. In some exemplary embodiments, the graft 140 may not extend past the second end 164, and one or more sutures 158 (FIG. 7) attached to the graft 140 may extend past the second end 164 instead, as will be understood by persons of ordinary skill in the art. In some exemplary embodiments, the graft 140 may be secured into the one or more grooves 170 prior to inserting the tibial graft spacer 152 into the tibial bone tunnel 160, and the graft 140 and the tibial graft spacer 152 may be inserted into the tibial bone tunnel 160 simultaneously. In other embodiments, a portion of the graft 140 may be inserted into the tibial bone tunnel 160 prior to inserting the tibial graft spacer 152 into the tibial bone tunnel 160. Further, in some exemplary embodiments, the tibial graft spacer 152 may be omitted. It is to be understood that the tibial graft spacer 152 may be inserted into the tibial tunnel 160 from either side of the tibial tunnel 160, for example.

The one or more sutures 158 attached to the graft 140 are passed through the tibial bone tunnel 160 such that the sutures 158 extend past an end of the tibial bone tunnel 160, for example. The sutures 158 may be passed through the one or more suture notches 182 such that the sutures 158 extend past the second end 174 of the tibial fixation implant 154, as shown in FIG. 7.

The first end 172 of the tibial fixation implant 154 is inserted into the tibial bone tunnel 160, such that the outer side 176 engages the tibial bone tunnel 160, and the flange 178 sits against, adjacent to, or slightly above the surface of the tibia. One or more washers (not shown), seals (not shown), or other implants (not shown) may be positioned between the flange 178 and the tibia, as will be understood by persons of ordinary skill in the art.

The sutures 158 may be tensioned at the appropriate tension, and one or more knots may be tied to secure the sutures 158 to the tibial fixation implant 154 at any desired tension. Any excess portions of the one or more sutures 158 may be trimmed and removed as needed or desired.

During body movements, as movement-related tension is applied to the graft 140, such tension is transferred as force to the bridge 104. The bridge 104 is at least partially compressed or deformed by the applied tension or force, which causes the first arm 102a and the second arm 102b to pivot about the bridge 104 relative to one another. Due to the direction of the tension or force being from the leading ends 108a and 108b towards the trailing ends 106a and 106b, the leading ends 108a and 108b will tend to move towards one another (FIG. 2) and the trailing ends 106a and 106b will tend to move away from one another (FIG. 2), for example. This scissor-like pivoting of the first arm 102a and the second arm 102b about the bridge 104 may cause the one or more bone-engaging protrusions 120a and 120b to transfer some of the force to the femoral bone tunnel 118 and substantially prevent backing out of the graft anchor 100. Further, the outer side 112a and the outer side 112b transfer a portion of the force to the femoral bone tunnel 118 by distributing such force over the outer side 112a and the outer side 112b, respectively. Such symmetrical force distribution over several areas inside the femoral bone tunnel 118 may allow for securely retaining the graft anchor 100 inside the femoral bone tunnel 118 without causing any unnecessary trauma or damage to the bone by concentrating the force onto a single point or narrow area of the femoral bone tunnel 118, for example.

It is to be understood that a method according to the inventive concepts disclosed herein may utilize the tibial portal, the antero-medial portal, the lateral portal, or any other suitable portal or incision, for example.

As will be appreciated by persons of ordinary skill in the art, the graft anchor 100' may function substantially similarly to the graft anchor 100 as described above. Further, the graft anchor 100' may be implemented with a graft fixation system substantially similar to the graft anchor system 150 as described above.

While the inventive concepts disclosed herein have been described in connection with the exemplary embodiments of the various figures, they are not limited thereto and it is to be understood that other similar embodiments may be used or modifications and additions may be made to the described embodiments for performing the same function of the inventive concepts disclosed herein without deviating therefrom. Therefore, the inventive concepts disclosed herein should not be limited to any single embodiment, but rather should be construed in breadth and scope in accordance with the appended claims. Also, the appended claims should be construed to include other variants and embodiments of the inventive concepts disclosed herein, which may be made by those skilled in the art without departing from the broad scope thereof.

What is claimed is:

1. A graft anchor, comprising:
   a first arm having a leading end, a trailing end, an inner surface, and an outer bone contactable surface;
   a second arm having a leading end, a trailing end, an inner surface, and an outer bone contactable surface;
   a resilient bridge extending between the inner surface of the first arm and the inner surface of the second arm to space apart the first arm and the second arm, the resilient bridge defining a graft receiving pathway between the inner surfaces of the first and second arms, the graft receiving pathway having a predetermined sealing dimension selected according to the size of the graft; and
   wherein the resilient bridge defines a deflection point about which a force acting upon the resilient bridge in a direction from the leading end to the trailing end causes the leading ends of the first and second arms to move toward one another and the trailing ends of the first and second arms to move away from each other.

2. The graft anchor of claim 1, wherein each of the first arm and the second arm has at least one bone engaging protrusion extending from the outer surface thereof at a location lateral to the resilient bridge such that the bone engaging protrusions move away from one another when the force is applied to the bridge.

3. The graft anchor implant of claim 2, wherein the bone engaging protrusions extend from the outer surface of the first arm and the second arm in a direction away from the trailing end of the first and second arms.

4. The graft anchor of claim 2, wherein, measured in a direction from the leading end to the trailing end of the first and second arms, the bone engaging protrusion ends a predetermined distance before the trailing ends.

5. The graft anchor of claim 1, wherein the resilient bridge is located in a region adjacent the trailing ends of the first and second arms.

6. The graft anchor of claim 1, wherein the graft receiving pathway has:
   a first channel defined by the inner surfaces of the first and second arms and a first surface of the resilient bridge; and
   a second channel defined by the inner surfaces of the first and second arms and a second surface of the resilient bridge, the second surface located on a side of the resilient bridge opposite to the side on which the first surface is located,
   wherein the sealing dimensions of the first and second channels are chosen to receive a graft therein in such a way that the graft and the graft anchor cooperate to form a seal in the entrance of a bone tunnel.

7. The graft anchor of claim 6, wherein the resilient bridge defines a bearing surface between the first and second channels upon which the force acts.

8. The graft anchor of claim 1, wherein the resilient bridge and the inner surfaces of the first and second arms define a smooth graft receiving surface.

9. The graft anchor of claim 1, wherein the first arm has at least one hole extending through the first arm from the inner surface to the outer surface between an upper side of the resilient bridge and the leading end of the first arm.

10. The graft anchor of claim 9, wherein the second arm has at least one hole extending through the second arm from the inner surface to the outer surface between the upper side of the resilient bridge and the leading end of the second arm.

11. The graft anchor of claim 1, wherein the outer surfaces of each of the first and second arms are configured to substantially conform to the contour of a bone tunnel and have a plurality of serrations formed thereon adapted for gripping engagement with the bone tunnel.

12. A graft anchoring system, comprising:
a graft anchor comprising:
- a first arm having a leading end, a trailing end, an inner surface, and an outer bone contactable surface;
- a second arm having a leading end, a trailing end, an inner surface, and an outer bone contactable surface; and
- a resilient bridge extending between the inner surface of the first arm and the inner surface of the second arm to space apart the first arm and the second arm, the resilient bridge defining a graft receiving pathway between the inner surfaces of the first and second arms,
- wherein the resilient bridge defines a deflection point about which a force acting upon the resilient bridge in a direction from the leading end to the trailing end causes the leading ends of the first and second arms to move toward one another and the trailing ends of the first and second arms to move away from each other;

a tibial graft spacer having a first end, a second end, and an outer surface configured to substantially conform to the contour of a tibial bone tunnel along a length of the outer surface from the first end to the second end, the outer surface having a plurality of serrations formed thereon adapted for gripping engagement with the tibial bone tunnel; and a tibial fixation implant having a first end, a second end, and an outer surface configured to substantially conform to the contour of the tibial bone tunnel, and a flange having a first diameter larger than a diameter of the tibial bone tunnel.

13. A method for graft anchoring, comprising:
forming a bone tunnel;
capturing a graft with a graft anchor comprising:
- a first arm having a leading end, a trailing end, an inner surface, and an outer bone contactable surface;
- a second arm having a leading end, a trailing end, an inner surface, and an outer bone contactable surface; and
- a resilient bridge extending between the inner surface of the first arm and the inner surface of the second arm to space apart the first arm and the second arm, the resilient bridge defining a graft receiving pathway between the inner surfaces of the first and second arms,
- wherein the resilient bridge defines a deflection point about which a force acting upon the resilient bridge in a direction from the leading end to the trailing end causes the leading ends of the first and second arms to move toward one another and the trailing ends of the first and second arms to move away from each other;

fixing the graft anchor and the graft in the bone tunnel; and
sealing an entrance into the tunnel with the trailing ends of the first and second arms and the graft arranged in the graft receiving pathway.

* * * * *